(12) United States Patent
Arul et al.

(10) Patent No.: US 7,897,613 B2
(45) Date of Patent: Mar. 1, 2011

(54) CRYSTALLINE POLYMORPHS OF CLOPIDOGREL

(75) Inventors: Ramakrishnan Arul, Maharashtra (IN); Ajay Singh Rawat, Maharashtra (IN); Maheshkumar Gadakar, Maharashtra (IN); Rajesh Rao, Maharashtra (IN); Abhinay Pise, Maharashtra (IN); Jason Gray, Hertfordshire (GB)

(73) Assignee: Generics [UK] Limited, Potters Bar, Hertfordshire (GB)

( * ) Notice: Subject to any disclaimer, the term of this patent is extended or adjusted under 35 U.S.C. 154(b) by 411 days.

(21) Appl. No.: 10/571,419

(22) PCT Filed: Sep. 9, 2004

(86) PCT No.: PCT/GB2004/003867
§ 371 (c)(1), (2), (4) Date: May 31, 2007

(87) PCT Pub. No.: WO2005/026174
PCT Pub. Date: Mar. 24, 2005

(65) Prior Publication Data
US 2007/0281964 A1    Dec. 6, 2007

(30) Foreign Application Priority Data
Sep. 11, 2003    (GB) .................... 0321256.0

(51) Int. Cl.
C07D 495/04    (2006.01)
A61K 31/4365    (2006.01)
A61P 7/02    (2006.01)

(52) U.S. Cl. ........................ 514/301; 546/114
(58) Field of Classification Search ............ 546/114; 514/301
See application file for complete search history.

(56) References Cited

U.S. PATENT DOCUMENTS

| | | | |
|---|---|---|---|
| 4,847,265 A | | 7/1989 | Badore et al. |
| 6,117,866 A | * | 9/2000 | Bondinell et al. ........... 514/221 |
| 6,180,793 B1 | | 1/2001 | Bakonyi et al. |
| 6,248,363 B1 | * | 6/2001 | Patel et al. ............ 424/497 |
| 6,429,210 B1 | | 8/2002 | Bousquet et al. |

FOREIGN PATENT DOCUMENTS

| | | |
|---|---|---|
| EP | 0 281 459 A1 | 7/1988 |
| WO | WO 03/066637 A1 | 8/2003 |
| WO | WO 2005/068471 A1 | 7/2005 |
| WO | WO 2005/103058 A1 | 11/2005 |

OTHER PUBLICATIONS

Umemura et al., Thrombosis research, (Nov. 1, 1995) vol. 80, No. 3, pp. 209-216.*
Mino R. Caira, "Crystalline Polymorphism of Organic Compounds," *Topics in Current Chemistry*, vol. 198, pp. 163-208 (1998).
"*PLAVIX*," Monthly Index of Medical Specialties, Aug. 2003, p. 72.
Loscalzo, et al., "Thrombosis and Hemorrhage", $3^{rd}$ ed., 2003, pp. 933-935.

* cited by examiner

*Primary Examiner* — D. Margaret Seaman
*Assistant Examiner* — Niloofar Rahmani
(74) *Attorney, Agent, or Firm* — Wolf, Greenfield & Sacks, P.C.

(57) ABSTRACT

The present invention relates to novel crystalline forms of the platelet aggregation inhibitor (+)-(S)-methyl-2-(2-chlorophenyl)-(6,7-dihydro-4H-thieno[3,2-c]pyrid-5-yl)acetate, clopidogrel (1), in the form of hydrogen bromide salts, identified as polymorph forms 1, 2 and 3. The present invention further relates to processes for preparing such forms, pharmaceutical compositions comprising such forms, and uses for such forms and compositions. The pharmaceutical compositions may be used, in particular, for inhibiting platelet aggregation or for treating, preventing or managing thrombosis, atherothrombosis, an atherothrombotic event, ischaemic stroke, myocardial infarction, non-Q-wave myocardial infarction, atherosclerosis, peripheral arterial disease, or unstable angina. The present invention also relates to methods of treating said disorders. Formula (1).

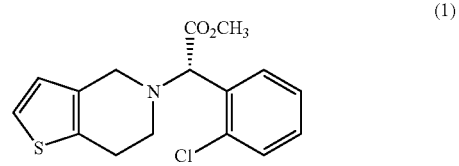

(1)

49 Claims, 5 Drawing Sheets

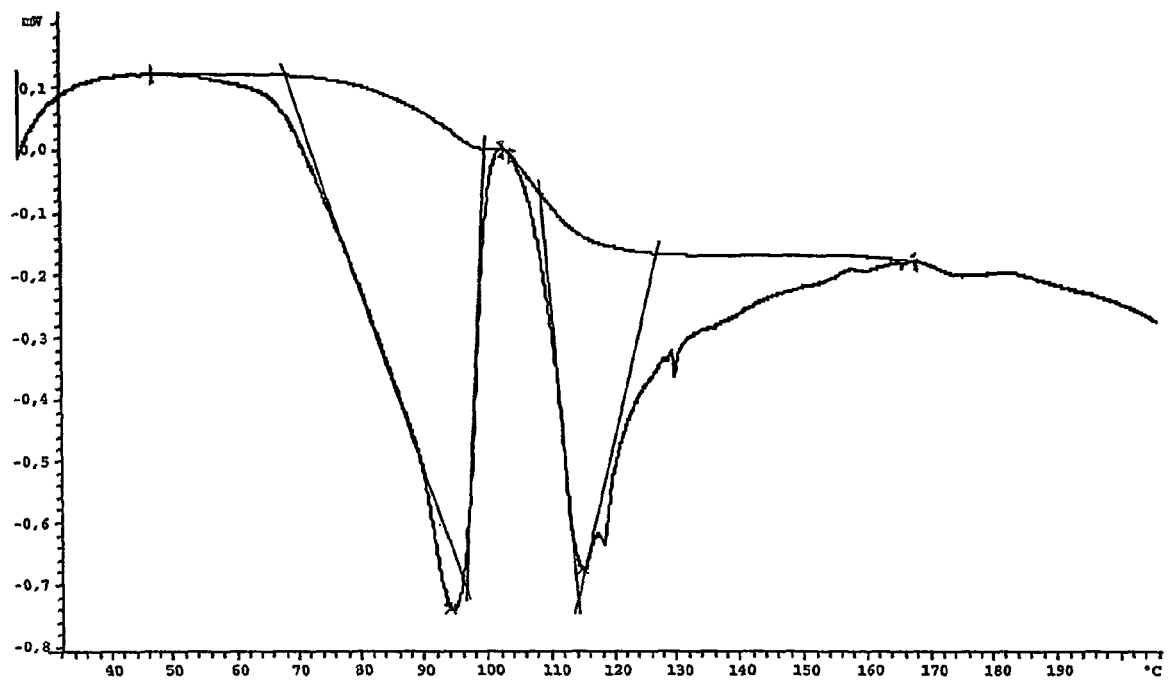
Figure One
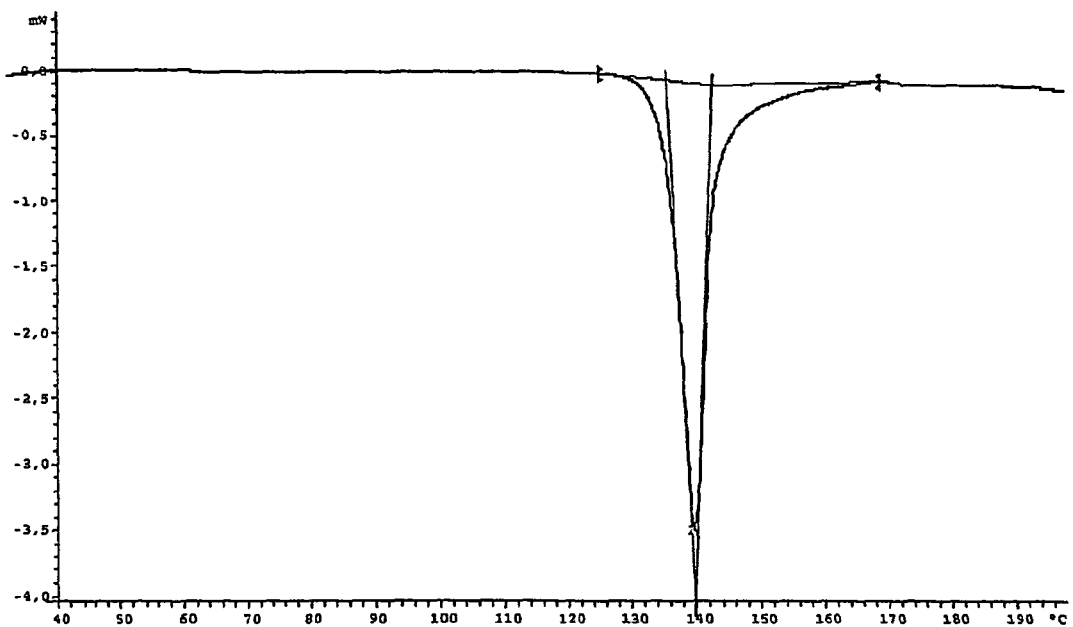
Figure Two

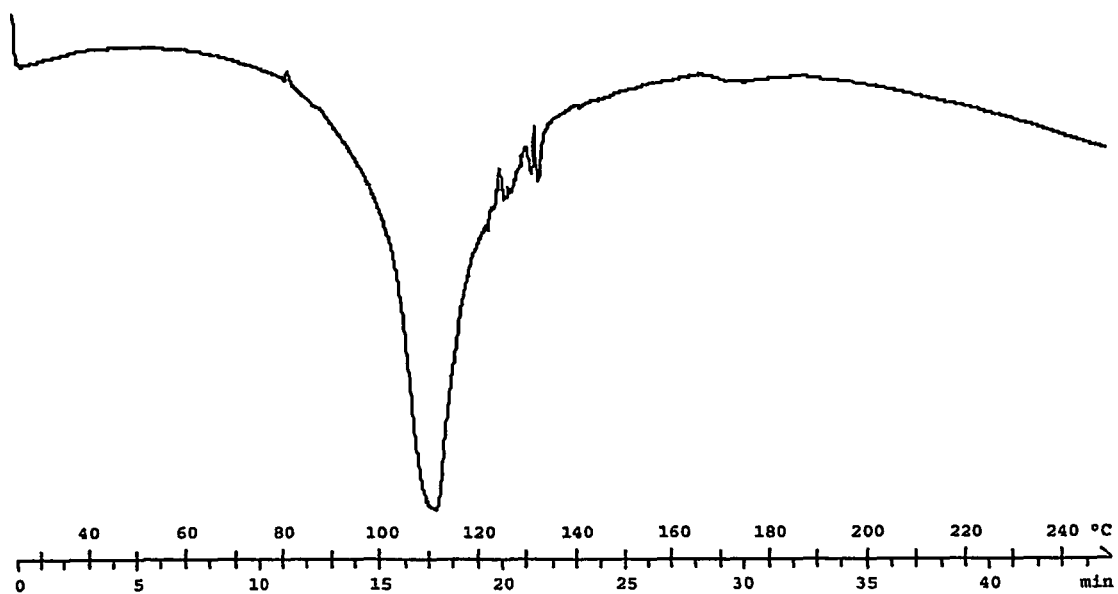
Figure Three
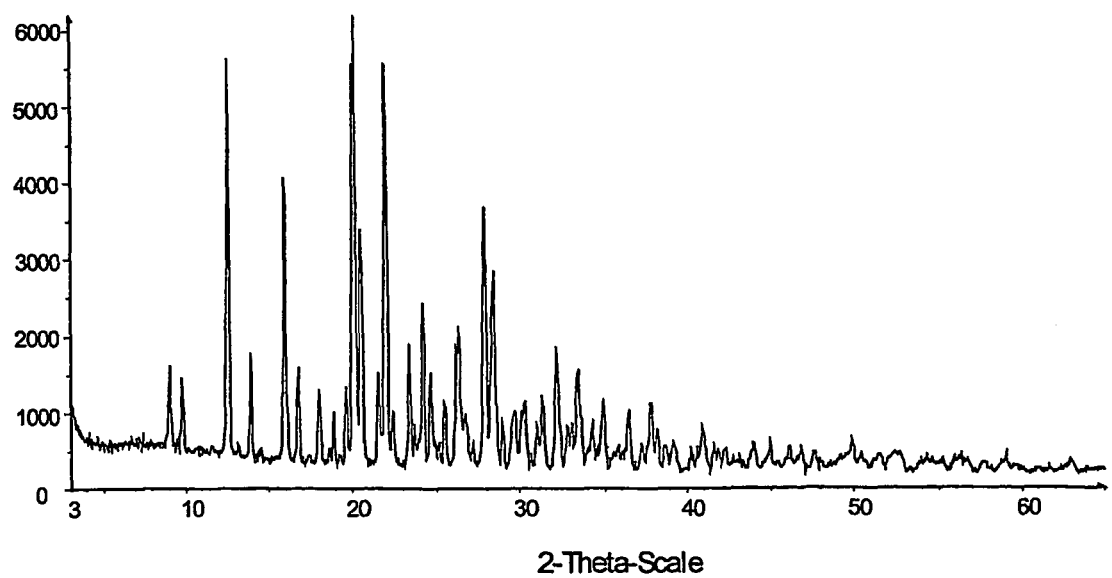
Figure Four

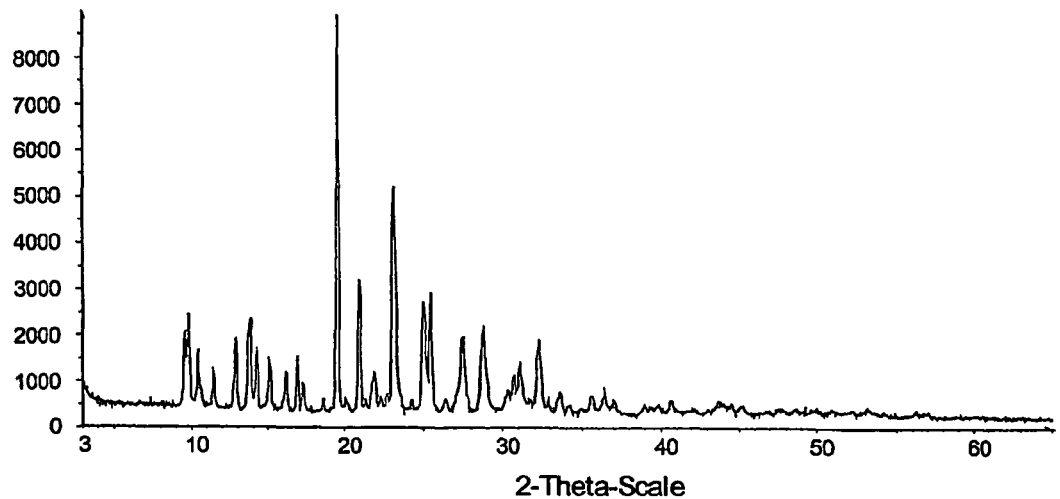
Figure Five
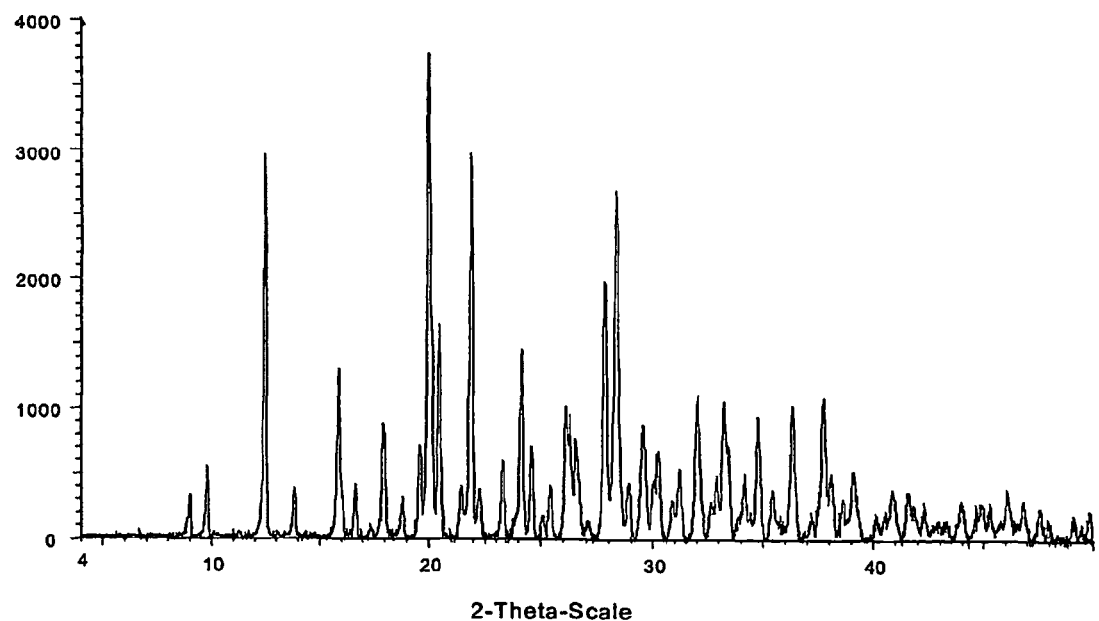
Figure Six

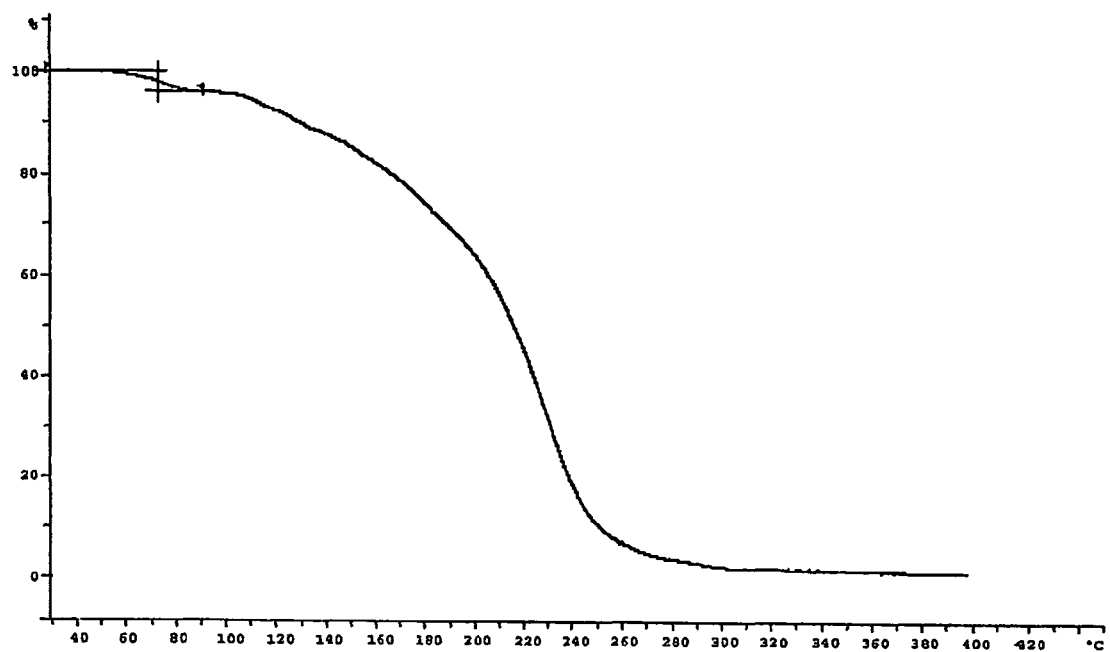
Figure Seven
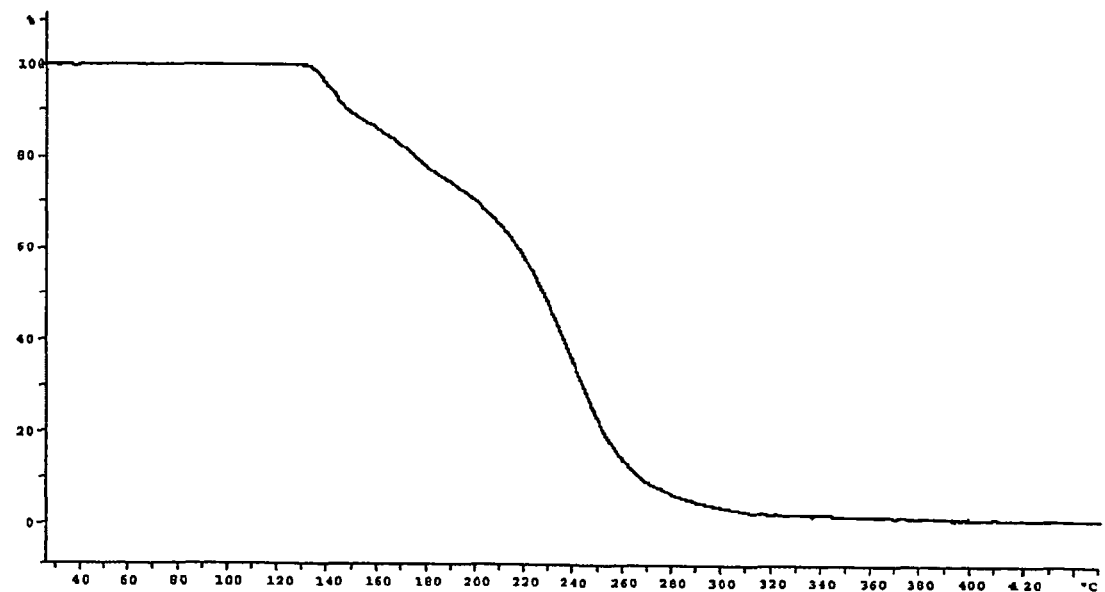
Figure Eight

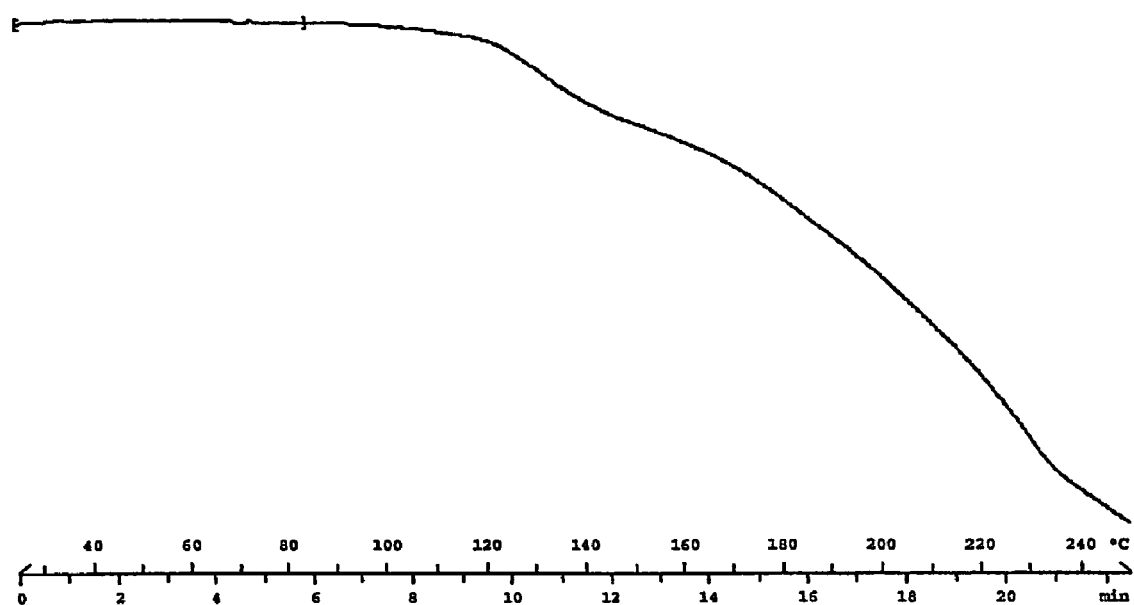
Figure Nine

CRYSTALLINE POLYMORPHS OF CLOPIDOGREL

RELATED APPLICATIONS

This application is a national stage filing under 35 U.S.C. §371 of international application PCT/GB2004/003867, filed Sep. 9, 2004, which was published under PCT Article 21(2) in English.

BACKGROUND ART

The present invention relates to novel crystalline forms of the platelet aggregation inhibitor (+)-(S)-methyl-2-(2-chlorophenyl)-(6,7-dihydro-4H-thieno[3,2-c]pyrid-5-yl)acetate, clopidogrel (1), in the form of hydrogen bromide salts. The present invention further relates to processes for preparing such forms, pharmaceutical compositions comprising such forms, and uses for such forms and compositions.

The pharmaceutical compositions may be used, in particular, for inhibiting platelet aggregation or for treating, preventing or managing thrombosis, atherothrombosis, an atherothrombotic event, ischaemic stroke, myocardial infarction, non-Q-wave myocardial infarction, atherosclerosis, peripheral arterial disease, or unstable angina. The present invention also relates to methods of treating said disorders.

TECHNICAL FIELD

The manufacturing process for many pharmaceuticals is hindered by the fact that the organic compound, which is the active drug substance, has handling difficulties during the manufacturing process and undesirable properties being imparted to the final drug or dosage form. In addition it can be difficult to control the polymorphic form of the active drug substance throughout the manufacturing process.

Previous preparations of clopidogrel (1) are reported in patent applications EP 0 420 706, EP 0 099 802, WO 98/51689, WO 98/51682, WO 98/51681, EP 0 466 569 and EP 0 281 459.

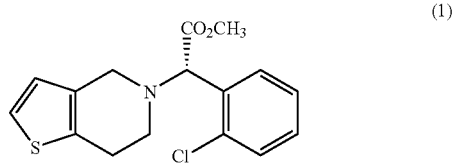

(1)

Clopidogrel is currently marketed as the hydrogen sulfate salt and polymorphic forms of this hydrogen sulfate salt have been reported in WO 99/65915. However, to date there have been no reports of polymorphs of the hydrogen bromide salt of clopidogrel.

SUMMARY OF THE INVENTION

It is an object of the present invention to provide clopidogrel in a solid crystalline form that affords the compound improved handling properties and/or improved properties as a pharmaceutical agent and enables control of the polymorphic form during manufacturing.

Accordingly, a first aspect of the present invention provides clopidogrel hydrogen bromide in polymorph form 1 (hydrate). Preferably the clopidogrel hydrogen bromide in polymorph form 1 has a DSC trace substantially as shown in Figure One, an XRPD spectrum substantially as shown in Figure Four, and/or TGA data substantially as shown in Figure Seven.

A second aspect of the present invention provides clopidogrel hydrogen bromide in polymorph form 2 (anhydrate). Preferably the clopidogrel hydrogen bromide in polymorph form 2 has a DSC trace substantially as shown in Figure Two, an XRPD spectrum substantially as shown in Figure Five, and/or TGA data substantially as shown in Figure Eight.

A third aspect of the present invention provides clopidogrel hydrogen bromide in polymorph form 3 (anhydrate). Preferably the clopidogrel hydrogen bromide in polymorph form 3 has a DSC trace substantially as shown in Figure Three, an XRPD spectrum substantially as shown in Figure Six, and/or TGA data substantially as shown in Figure Nine.

Preferably the clopidogrel hydrogen bromide in polymorph form 1, 2 or 3 is in particulate form. Preferably the clopidogrel hydrogen bromide in polymorph form 1, 2 or 3 is substantially pure.

In the context of the present application, the term "substantially pure" clopidogrel hydrogen bromide in polymorph form 1 means that the clopidogrel hydrogen bromide in polymorph form 1 comprises less than 20% of other crystalline or amorphous forms of clopidogrel hydrogen bromide, preferably less than 15%, more preferably less than 10%, more preferably less than 5%, more preferably less than 2%, more preferably less than 1%, and even more preferably less than 0.5%. The term "substantially pure" also means that the clopidogrel hydrogen bromide in polymorph form 1 comprises less than 3% of other impurities, preferably less than 2%, more preferably less than 1%, and even more preferably less than 0.5%. The term "substantially pure" is defined accordingly in the context of clopidogrel hydrogen bromide in polymorph form 2 or polymorph form 3.

Preferably the clopidogrel hydrogen bromide in polymorph form 1, 2 or 3 is for use as a medicament. Preferably the medicament is for inhibiting platelet aggregation or for treating, preventing or managing thrombosis, atherothrombosis, an atherothrombotic event, ischaemic stroke, myocardial infarction, non-Q-wave myocardial infarction, atherosclerosis, peripheral arterial disease, or unstable angina.

Fourth, fifth and sixth aspects of the invention provide processes for the respective preparation of the clopidogrel hydrogen bromide of the first, second and third aspects of the invention.

The compounds of the invention are preferably preparable or prepared by a process comprising crystallisation from a solution in an organic solvent or solvents. Said process, in an embodiment, also comprises the step of drying the precipitate to provide a crystalline form in accordance with the first, second or third aspect of the invention. The compound can be dried under conventional vacuum drying conditions, for example, under a vacuum of down to 50, 40, 35, 30, 25 or 20 mmHg, preferably 30 mmHg, and at a temperature of up to 20, 25, 30, 35, 40, 45, 50, 55 or 60° C., preferably 45° C. Preferably the organic solvent is polar, miscible with water, dipolar, and/or aprotic. Optionally the organic solvent comprises a plurality or mixture of solvent compounds. The organic solvent may be 2-propanol, diisopropyl ether, t-butylmethyl ether, dichloromethane, methanol, and/or ethanol.

Clopidogrel hydrogen bromide in polymorph form 1 is preferably prepared by recrystallisation from a mixture of 2-propanol and diisopropyl ether, preferably in a 2-propanol:diisopropyl ether ratio of from 50:50 to 70:30, preferably about 60:40. Preferably the recrystallisation is carried out at 20-35° C. for 1-6 hours followed by 0-15° C. for 0.1-4 hours;

more preferably the recrystallisation is carried out at 25-30° C. for 1.5-3 hours followed by 5-10° C. for 0.5-1.5 hours.

Clopidogrel hydrogen bromide in polymorph form 2 is preferably prepared by recrystallisation from a mixture of 2-propanol and diisopropyl ether, preferably in a 2-propanol: diisopropyl ether ratio of from 1:10 to 40:60, preferably from 10:90 to 30:70. Preferably the recrystallisation is carried out at 20-35° C. for 1-6 hours; more preferably the recrystallisation is carried out at 25-30° C. for 1.5-3 hours.

Alternatively, clopidogrel hydrogen bromide in polymorph form 2 may be prepared by recrystallisation from t-butylmethyl ether. Preferably the recrystallisation is carried out at 20-35° C. for 0.5-4 hours; more preferably the recrystallisation is carried out at 27-32° C. for 0.5-2 hours.

Clopidogrel hydrogen bromide in polymorph form 3 is preferably prepared by recrystallisation from a mixture of methanol or ethanol with water, preferably in an alcohol: water ratio of from 5:95 to 20:80, preferably about 10:90. Preferably the recrystallisation is carried out at 2-10° C. for 8-20 hours; more preferably the recrystallisation is carried out at 3-8° C. for 10-15 hours.

Compounds in accordance with the first, second and third aspects of the invention can be used to advantage in the preparation of pharmaceutical dosage or drug forms. Accordingly, in further aspects, the present invention provides a method of preparing a pharmaceutical dosage form that utilizes compounds in accordance with the first, second and third aspects of the invention.

The present invention also provides a pharmaceutical composition prepared or preparable by such a method. The pharmaceutical composition of the present invention may be for immediate, sustained or delayed release. The composition is preferably solid and comprises a compound in accordance with the first, second or third aspect of the invention, in addition to one or more conventional pharmaceutically acceptable carrier(s), excipient(s) or diluent(s). Preferred pharmaceutical compositions in accordance with the invention include tablets, capsules and the like.

The pharmaceutical composition of the present invention can be administered by oral, parental (including intravenous, subcutaneous, intramuscular, intradermal, intratracheal, intraperitoneal, intraarticular, intracranial and epidural), transdermal, airway (aerosol), rectal, vaginal or topical (including buccal, mucosal and sublingual) administration. Preferably the composition is for oral administration.

For oral administration, the pharmaceutical composition of the invention will generally be provided in the form of tablets, capsules, hard or soft gelatine capsules, caplets, troches or lozenges, as a powder or granules, or as an aqueous solution, suspension or dispersion. Solutions, suspensions and dispersions may be prepared from powder or granules of clopidogrel hydrogen bromide in polymorph form 1, 2 or 3. Preferably the composition is in the form of tablets or capsules.

Tablets for oral use may include clopidogrel hydrogen bromide in polymorph form 1, 2 or 3 mixed with pharmaceutically acceptable excipients such as inert diluents, disintegrating agents, binding agents, lubricating agents, sweetening agents, flavouring agents, colouring agents and preservatives. Suitable excipients are mannitol, macrogol, microcrystalline cellulose, hydrogenated castor oil, and low substituted hydroxypropylcellulose. Tablets can be prepared by conventional techniques, including direct compression, wet granulation and dry granulation. If desired, the tablets may be coated with materials such as hypromellose, lactose, triacetin, and/or carnauba wax.

Capsules for oral use include hard gelatine capsules in which clopidogrel hydrogen bromide in polymorph form 1, 2 or 3 is mixed with a solid diluent, and soft gelatine capsules wherein clopidogrel hydrogen bromide in polymorph form 1, 2 or 3 is mixed with water or an oil such as peanut oil, liquid paraffin or olive oil.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds of the present invention will generally be provided in a sterile aqueous solution or suspension, buffered to an appropriate pH and isotonicity. Such solutions and suspensions may be prepared from powder or granules of clopidogrel hydrogen bromide in polymorph form 1, 2 or 3. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For topical and transdermal administration, the compounds of the invention will generally be provided in the form of ointments, cataplasms (poultices), pastes, powders, dressings, creams, plasters or patches.

Suitable suspensions and solutions can be used in inhalers for airway (aerosol) administration. Such suspensions and solutions may be prepared from powder or granules of clopidogrel hydrogen bromide in polymorph form 1, 2 or 3.

Preferably the pharmaceutical composition is in unit dosage form comprising clopidogrel hydrogen bromide in polymorph form 1, 2 or 3 in an amount of from 1 mg to 300 mg with respect to the free base, preferably in an amount of from 5 mg to 200 mg, more preferably in an amount of from 10 mg to 125 mg, and mote preferably in an amount of from 50 mg to 100 mg.

The clopidogrel hydrogen bromide of the present invention is effective over a wide dosage range, the actual dose administered being dependent on the condition being treated. For example, in the treatment of adult humans, dosages from 1 mg to 300 mg, preferably from 10 mg to 125 mg, more preferably from 50 mg to 100 mg with respect to the free base per day may be used. The desired dose is normally presented once a day, but may be dosed as two, three, four or more sub-doses administered at appropriate intervals throughout the day.

Preferably the pharmaceutical composition of the present invention is for inhibiting platelet aggregation or for treating, preventing or managing thrombosis, atherothrombosis, an atherothrombotic event, ischaemic stroke, myocardial infarction, non-Q-wave myocardial infarction, atherosclerosis, peripheral arterial disease, or unstable angina.

In further aspects, the present invention provides a method of inhibiting platelet aggregation, comprising administering an effective amount of clopidogrel hydrogen bromide in polymorph form 1, 2 or 3 to a patient in need thereof. The present invention also provides a method of treating, preventing or managing a condition selected from thrombosis, atherothrombosis, an atherothrombotic event, ischaemic stroke, myocardial infarction, non-Q-wave myocardial infarction, atherosclerosis, peripheral arterial disease, and unstable angina, comprising administering an effective amount of clopidogrel hydrogen bromide in polymorph form 1, 2 or 3 to a patient in need thereof. Preferably the patient is a human. Preferably the amount of clopidogrel hydrogen bromide administered is from 10 mg to 125 mg, preferably from 50 mg to 100 mg with respect to the free base per day.

In a further aspect of the invention, there is provided the use of a compound in accordance with the first, second or third aspect of the invention for the manufacture of a medicament for the inhibition of platelet aggregation and consequently the treatment, prevention and/or management of such diseases as thrombosis, atherothrombosis, an atherothrombotic event, ischaemic stroke, myocardial infarction, non-Q-wave myocardial infarction, atherosclerosis, peripheral arterial disease or unstable angina.

The compounds in accordance with the first, second and third aspects of the invention may also be useful as precursors to other novel or known polymorphic forms of clopidogrel that may be useful in the preparation of pharmaceutical products. Alternatively, the compounds in accordance with the first, second and third aspects of the invention may be used to prepare other desired polymorphic forms of clopidogrel hydrogen sulfate in a more controllable manner. The present invention therefore provides a process for preparing a polymorphic form of clopidogrel hydrogen sulfate, comprising the step of using clopidogrel hydrogen bromide in polymorph form 1, 2 or 3.

The present invention is illustrated, but in no way limited, by the following examples and figures.

BRIEF DESCRIPTION OF THE FIGURES

Figure One is a DSC trace of polymorph form 1 clopidogrel hydrogen bromide.
Figure Two is a DSC trace of polymorph form 2 clopidogrel hydrogen bromide.
Figure Three is a DSC trace of polymorph form 3 clopidogrel hydrogen bromide.
Figure Four is an XRPD spectrum of polymorph form 1 clopidogrel hydrogen bromide.
Figure Five is an XRPD spectrum of polymorph form 2 clopidogrel hydrogen bromide.
Figure Six is an XRPD spectrum of polymorph form 3 clopidogrel hydrogen bromide.
Figure Seven shows TGA data for polymorph form 1 clopidogrel hydrogen bromide.
Figure Eight shows TGA data for polymorph form 2 clopidogrel hydrogen bromide.
Figure Nine shows TGA data for polymorph form 3 clopidogrel hydrogen bromide.

DETAILED DESCRIPTION OF THE INVENTION/EXAMPLES (±)-2-(2-Chlorophenyl)-(6,7-dihydro-4H-thieno[3,2-c]pyrid-5-yl)acetonitrile To a mixture of methanol (2.50 l) and water (250 ml) was charged 4,5,6,7-tetrahydro-thieno[3,2-c]pyridine hydrochloride (500 g; 2.85 mol) with stirring. After stirring for 10 minutes, sodium cyanide (153.0 g; 3.12 mol) was added and stirred further for 40 minutes. 2-Chlorobenzaldehyde (392.1 g; 2.79 mol) was added slowly to this reaction mixture between 23-28° C. over a period of 1.5 hours. After the addition was over, the flask was heated in an oil bath between 40-50° C. and maintained at this temperature for 4.5 hours. After cooling the reaction mixture to 25-30° C., 5% sodium metabisulfite solution (250 ml) was added and stirred for 1 hour at this temperature range. To the resulting slurry, water (7.5 l) was added and stirred for 1 hour at 25-30° C. The off-white solid thus formed was filtered, washed with a 1:1 mixture of methanol: water (2.5 l) and the wet cake was dried at 75° C. under vacuum (pressure: −0.8 kg/cm$^2$) for 10 hours to obtain the product as an off-white solid. Yield: 719.0 g (87.4%). mp: 124-126.5° C. The product was identified by IR spectrum, $^1$H and $^{13}$C NMR investigation.

(±)-2-(2-Chlorophenyl)-(6,7-dihydro-4H-thieno[3,2-c]pyrid-5-yl)acetamide (±)-2-(2-Chlorophenyl)-(6,7-dihydro-4H-thieno[3,2-c]pyrid-5-yl)acetonitrile (713 g; 2.46 mol) was added to methanol (3.505 l) at 23-28° C. with stirring. To this slurry, potassium carbonate (170 g; 1.23 mol) was added followed by dimethyl sulfoxide (263 ml; 3.7 mol). The contents were heated between 30-40° C. and 30.0% aqueous hydrogen peroxide solution (382 ml; 3.70 mol) was added between 40-50° C. slowly over a period of 3 hours. After the addition was over, the reaction mixture was maintained at this temperature for a further 2 hours, after which the reaction was brought to 20-30° C. 35% Hydrochloric acid (213.0 ml) in water (10.7 l) was added slowly to the reaction mixture over a period of 1 hour 15 minutes. After stirring for 1 hour, the solid formed was filtered and washed with a 1:1 methanol: water mixture (3.565 l). The isolated solid was dried in a vacuum oven at 75-80° C. for a period of 12 hours. Yield: 716 g (94.72%). mp: 124-126° C. The product was identified by IR spectrum, $^1$H and $^{13}$C NMR investigation.

(+)-(1S)-Camphor-10-sulfonic acid salt of (S)-2-(2-Chlorophenyl)-(6.7-dihydro-4H-thieno[3,2-c]pyrid-5-yl)acetamide (a) To a stirred slurry of (±)-2-(2-chlorophenyl)-6,7-dihydro-4 H-thieno[3,2-c]pyrid-5-yl)acetamide (710 g; 2.315 mol) in acetone (3.56 l) and methanol (0.355 l) maintained at 23-28° C. was added a solution of (+)-(1S)-camphor-10-sulfonic acid (270 g; 1.16 mol) dissolved in acetone (1.44 l) over a period of 1 hour. After stirring for another hour, formic acid (98-100%; 53.8 g; 1.16 mol) was added all at once and stirred for 1 hour, after which the reaction mixture was cooled to 0-10° C. and kept at this temperature for another 1 hour 30 minutes. The solid thus formed was filtered and washed with acetone (1.44 l) and dried in a vacuum oven between 60-65° C. for a period of 6 hours. Yield: 470.0 g (38% by theory, based on the enantiomer content). mp: 194-208° C. $[\alpha]_D^{25}$: +41.5 (c=1.0 g/100 ml; methanol).

(b) Isolation of (±)-2-(2-Chlorophenyl)-(6,7-dihydro-4H-thieno[3,2-c]pyrid-5-yl)acetamide from the mother liquor obtained in step (a)

To the mother liquor obtained in step (a), 20% aqueous solution of sodium hydroxide (710 ml) was added at 26-27° C. with stirring. The reaction mixture was heated to 45-50° C. and maintained at that temperature for 5 hours. The reaction mixture was concentrated to ⅒ of its volume under vacuum. The resulting slurry was cooled to 30° C. and methanol (710 ml) was added followed by water (4.9 l) slowly to the reaction mixture over a period of 30 minutes. The pH of the reaction mass was adjusted to 7-7.5 by the addition of 15% hydrochloric acid solution (1.2 l). After stirring for an hour, the solid formed was filtered and washed with water (3.5 l). The isolated solid was dried in a vacuum oven (pressure: −0.8 kg/cm$^2$) between 75-80° C. for a period of 14 hours. Yield: 393 g. mp: 128-134° C.

(c) (±)-2-(2-Chlorophenyl)-(6,7-dihydro-4H-thieno[3,2-c]pyrid-5-yl)acetamide obtained in step (b) was converted to (+)-(1S)-camphor-10-sulfonic acid salt of (S)-2-(2-chlorophenyl)-(6,7-dihydro-4H-thieno[3,2-c]pyrid-5 -yl)acetamide by following the procedure mentioned in step (a). Yield: 240.0 g (36% by theory, based on the enantiomer content). mp: 202-210° C. $[\alpha]_D^{25}$: +47.5 (c=1.0 g/100 ml; methanol).

(d) The (+)-(1S)-camphor-10-sulfonic acid salt of (S)-2-(2-chlorophenyl)-(6,7-dihydro-4H-thieno[3,2-c]pyrid-5-yl) acetamide (700 g; 1.298 mol) obtained was charged into methanol (1.75 l) with stirring at 23-28° C. The contents were heated to 60° C. and the temperature was maintained at this temperature for 2 hours. To this clear solution, acetone (7.0 l) was added and the temperature was maintained at this temperature for 1 hour. The reaction mixture was cooled between 0-5° C. and stirred for another 1 hour and 30 minutes. The solid thus precipitated was filtered, washed with acetone (1.4 l) and dried between 60-65° C. under vacuum (−0.8 kg/cm²) for 7 hours. Yield: 545.0 g (77.85% by theory). mp: 210-218° C. $[\alpha]_D^{25}$: +51.69 (c=1.0 g/100 ml; methanol).

(+)-(S)-2-(2-Chlorophenyl)-(6,7-dihydro-4H-thieno[3,2-c]pyrid-5-yl)acetamide The crystallized (+)-(1S)-camphor-10-sulfonic acid salt of (S)-2-(2-chlorophenyl)-(6,7-dihydro-4H-thieno[3,2-c]pyrid-5-yl)acetamide (521.0 g; 0.966 mol) was charged into methanol (2.605 l) with stirring at 23-28° C. followed by water (1.042 l). To this clear solution, activated carbon (10.42 g) was added and the contents were stirred for 1.5 hours at this temperature. The activated carbon was filtered off by passing the contents of the flask through a bed of celite on a Buchner funnel and the residue in the funnel was washed with a water: methanol mixture (3:7; 0.521 l). To the combined filtrate, 2% (w/v) aqueous sodium bicarbonate solution (4.168 l) was added over a period of 30 minutes and stirred for 1 hour and 30 minutes. The solid precipitated was filtered, washed with methanol: water (2.084 l; 1:1 v/v) and dried under vacuum (−0.8 kg/cm²) for a period of 8 hours between 70-75° C. Yield: 284.0 g (95.8% by theory). mp: 154-156° C. $[\alpha]_D^{25}$: +39.5 (c=1.0 g/100 ml; methanol). The product was identified by IR spectrum, $^1$H and $^{13}$C NMR investigation.

(+)-(S)-Methyl-2-(2-chlorophenyl)-(6,7-dihydro-4H-thieno[3,2-c]pyrid-5-yl)acetate(clopidogrel)

Concentrated sulfuric acid (~98%; 496 ml; 9.30 mol) was charged into methanol (1.75 l) with sting between 25-38° C. followed by dimethyl sulfate (250 ml; 2.636 mol). The contents were heated to reflux for 3 hours, after which the reaction mixture was cooled to 40-50° C. and (+)-(S)-2-(2-chlorophenyl)-(6,7-dihydro-4H-thieno[3,2-c]pyrid-5yl) acetamide (500 g; 1.55 mol) was charged. The reaction mixture was heated to 65° C. and maintained between 65-66° C. for a period of 60 hours. The reaction mixture was cooled to 25-30° C. and poured into water (10.0 l) with stirring. Dichloromethane (5.0 l) was added, stirred for 1 hour, after which the organic layer was separated. To the aqueous layer dichloromethane (2.5 l) was added and stirred for 1 hour and the separated organic layer was combined with the earlier separated layer and washed with water (2.5 l). 5% (w/v) aqueous sodium bicarbonate solution (2.5 l) was added to this organic layer and stirred for a period of an hour and the separated organic layer was washed with 0.25% sulfuric acid (2.5 l) followed by water (2.5 l) and treated with activated carbon (40.0 g) for a period of 3 hours with stirring. The activated carbon was removed by filtration through a celite bed and the celite bed was washed with dichloromethane (1.0 l). This washing was coupled with the filtrate and the solvent removed under vacuum to yield (+)-(S)-2-(2-chlorophenyl)-(6,7-dihydro-4H-thieno[3,2-c]pyrid-5-yl)acetic acid methyl ester as a pale yellow oil. Yield: 380 g (73.0% by theory). The product was identified by IR spectrum, $^1$H and $^{13}$C NMR investigation.

(+)-(S)-Methyl-2-(2-chlorophenyl)-(6.7-dihydro-4H-thieno[3,2-c]pyrid-5-yl)acetate(clopidogrel)hydrogen bromide polymorph form 1

Method 1: To a stirred solution of (+)-(S)-methyl-2-(2-chlorophenyl)-(6,7-dihydro-4H-thieno[3,2-c]pyrid-5-yl)acetate (20 g; 0.062 mol) in 2 -propanol (60 ml) and diisopropyl ether (40 ml) was added ~47% aqueous hydrobromic acid solution (10.88 g; 0.0631 mol of HBr) with stirring between 20-26° C. over a period of 20 minutes. The contents were stirred for 2 hours and 30 minutes between 26 -28° C., cooled to 10° C. and maintained at this temperature for 30 minutes. The precipitated solid was filtered, washed twice with diisopropyl ether (20 ml each time) and dried in a vacuum oven between 45-50° C. for 4 hours.

The product was characterized by DSC and XRPD (see Figures One and Four respectively). TGA indicated that the product is a hydrate form (see Figure Seven). There are two peaks in the DSC trace indicating the evaporation of water followed by a peak indicating the anhydrate form (polymorph form 3).

Method 2: (+)-(S)-Methyl-2-(2-chlorophenyl)-(6,7-dihydro-4H-thieno[3,2-c]pyrid-5-yl)acetate hydrogen bromide (69 g) was charged into 2-propanol (760 ml) with stirring at 25-26° C. The contents were heated between 45-50° C. To this clear solution, activated carbon (3.7 g) was added and the reaction temperature was maintained at 38° C. for 1 hour. The contents were cooled to 26-28° C. The activated carbon was filtered off by passing the contents of the flask through a bed of celite on a Buchner flask and the residue in the funnel was washed with 2-propanol (140 ml). To the combined filtrate, diisopropyl ether (690 ml) was added and stirred for 2 hours at 26-27° C. The reaction contents were cooled to 0-5° C. and maintained at this temperature for 1 hour. The solid precipitated was filtered, washed twice with diisopropyl ether (140 ml each time) and dried in a vacuum oven between 45-50° C. for 5 hours. Yield: 57 g (82.6%).

(+)-(S)-Methyl-2-(2-chlorophenyl)-(6,7-dihydro-4H-thieno[3,2-c]pyrid-5-yl)acetate(clopidogrel)hydrogen bromide polymorph form 2

Method 1: (+)-(S)-Methyl-2-(2-chlorophenyl)-(6,7-dihydro-4H-thieno[3,2-c]pyrid-5-yl)acetate hydrogen bromide (220 g) was charged into 2-propanol (242 ml) with stirring at 25-26° C. The contents were heated to 50° C. To this clear solution, activated carbon (4.4 g) was added and the reaction temperature was maintained between 34-40° C. for 1 hour. The contents were cooled to 26-28° C. The activated carbon was filtered off by passing the contents of the flask through a bed of celite on a Buchner flask and the residue in the funnel was washed with 2-propanol (440 ml). To the combined filtrate, diisopropyl ether (2.2 l) was added and stirred for 2 hours at 26-27° C. The solid precipitated was filtered, washed twice with diisopropyl ether (440 ml each time) and dried in a vacuum oven between 45-50° C. for 5 hours. Yield: 147 g (66%).

Method 2: To a stirred solution of (+)-(S)-methyl-2-(2-chlorophenyl)-(6,7-dihydro-4H-thieno[3,2-c]pyrid-5-yl)acetic acid (22 g; 0.068 mol) in t-butylmethyl ether (110 ml) was added hydrogen bromide in acetic acid solution (~33%; 12.69 ml; 0.072 mol of HBr) with stirring between 20-26° C. over a period of 20 minutes. To the reaction mixture, 2-propanol (110 ml) was added and the reaction mixture was heated to 40° C. The contents were cooled to 30° C. and stirred for 45 minutes between 28-30° C. The precipitated solid was filtered, washed with t-butylmethyl ether: 2 -propanol (1:1; 44 ml) followed by t-butylmethyl ether (22 ml each time) and dried in a vacuum oven (−0.8 kg/cm$^2$) between 45-50° C. for 6 hours. Yield: 16 g (58%).

Method 3: To a stirred solution of (+)-(S)-methyl-2-(2-chlorophenyl)-(6,7-dihydro-4H-thieno[3,2-c]pyrid-5-yl)acetic acid (10 g; 0.031 mol) in dichloromethane (40 ml) was added ~47% aqueous hydrobromic acid solution (3.56 ml; 0.031 mol of HBr) with stirring between 20-21° C. over a period of 10 minutes. The contents were stirred for 3 hours between 26-27° C. The reaction mixture was dried over sodium sulfate and solvent was removed under vacuum and to the residue 2-propanol (40 ml) and diisopropyl ether (40 ml) were added. After stirring for 30 minutes the solid was filtered, washed twice with diisopropyl ether (20 ml each time) and dried in a vacuum oven between 45-50° C. for 4 hours. Yield: 10 g (80%).

Each method gave clopidogrel hydrogen bromide in polymorph form 2 as determined by DSC, XRPD and TGA (see Figures Two, Five and Eight)

(+)-(S)-Methyl-2-(2-chlorophenyl) -(6,7-dihydro-4H-thieno[3,2-c]pyrid-5-yl)acetate(clopidogrel)hydrogen bromide polymorph form 3

Clopidogrel hydrogen bromide polymorph form 3 was prepared by dissolving clopidogrel hydrogen bromide polymorph form 1 (5 g) in 5 ml of either methanol or ethanol. Once dissolved at room temperature (~22° C.), water (40 ml) was added to the solution and stirred. The initial precipitate formed was a sticky solid. This solid was filtered off and the remaining solution stored in a refrigerator overnight. The white crystals formed in this chilled solution were then filtered using a Buchner filter funnel and dried at 50° C. for one hour.

The crystals were then characterized using DSC, TGA and XRPD (See Figures Three, Six and Nine)

The invention claimed is:

1. Clopidogrel hydrogen bromide hydrate in polymorph form 1, wherein the compound has a differential scanning calorimetry trace substantially as shown in Figure One, an X-ray powder diffraction spectrum substantially as shown in Figure Four, and/or thermogravimetric analysis data substantially as shown in Figure Seven.

2. Clopidogrel hydrogen bromide anhydrate in polymorph form 2, wherein the compound has a differential scanning calorimetry trace substantially as shown in Figure Two, an X-ray powder diffraction spectrum substantially as shown in Figure Five, and/or thermogravimetric analysis data substantially as shown in Figure Eight.

3. Clopidogrel hydrogen bromide anhydrate in polymorph form 3, wherein the compound has a differential scanning calorimetry trace substantially as shown in Figure Three, an X-ray powder diffraction spectrum substantially as shown in Figure Six, and/or thermogravimetric analysis data substantially as shown in Figure Nine.

4. Clopidogrel hydrogen bromide hydrate as claimed in claim 1, wherein the clopidogrel hydrogen bromide hydrate is in particulate form.

5. Clopidogrel hydrogen bromide hydrate as claimed in claim 1, wherein the clopidogrel hydrogen bromide hydrate or anhydrate is substantially pure.

6. A process for preparing clopidogrel hydrogen bromide hydrate as claimed in claim 1, comprising the step of precipitating clopidogrel hydrogen bromide hydrate from a solution of clopidogrel hydrogen bromide in an organic solvent.

7. A process as claimed in claim 6, further comprising the step of drying the precipitate.

8. A process as claimed in claim 7, wherein the drying step comprises vacuum drying.

9. A process as claimed in claim 8, wherein the drying step comprises vacuum drying at a vacuum of down to 50, 40, 35, 30, 25 or 20 mm Hg and at a temperature of up to 20, 25, 30, 35, 40, 45, 50, 55 or 60° C.

10. A process as claimed in claim 6, wherein the organic solvent is polar, miscible with water, dipolar, and/or aprotic.

11. A process as claimed in claim 6, wherein the organic solvent comprises a plurality or mixture of solvent compounds.

12. A process as claimed in claim 6, wherein the organic solvent is 2-propanol, diisopropyl ether, t-butylmethyl ether, dichloromethane, methanol, and/or ethanol.

13. A pharmaceutical composition, comprising clopidogrel hydrogen bromide hydrate as claimed in claim 1.

14. A pharmaceutical composition as claimed in claim 13, further comprising a pharmaceutically acceptable carrier, excipient or diluent.

15. A pharmaceutical composition as claimed in claim 13, wherein the composition is for oral administration.

16. A pharmaceutical composition as claimed in claim 13, wherein the composition is in the form of a tablet or capsule.

17. A pharmaceutical composition as claimed in claim 16, wherein the composition is in the form of a tablet and further comprises mannitol, macrogol, microcrystalline cellulose, hydrogenated castor oil, and/or low substituted hydroxypropylcellulose.

18. A pharmaceutical composition as claimed in claim 17, wherein the tablet is coated with hypromellose, lactose, triacetin, and/or carnauba wax.

19. A pharmaceutical composition as claimed in claim 13, wherein the composition is in unit dosage form comprising clopidogrel hydrogen bromide hydrate in an amount of from 10 mg to 125 mg with respect to the free base.

20. A method of inhibiting platelet aggregation, comprising administering an effective amount of clopidogrel hydrogen bromide hydrate as claimed in claim 1 to a patient in need thereof.

21. A method as claimed in claim 20, wherein the patient is a human.

22. A method as claimed in claim 20, wherein the amount of clopidogrel hydrogen bromide hydrate administered is from 10 mg to 125 mg with respect to the free base per day.

23. A process for preparing a polymorphic form of clopidogrel hydrogen sulfate, comprising the step of treating a clopidogrel hydrogen bromide hydrate as claimed in claim 1 with a chemical species to replace the bromide ion with a sulfate ion, thereby forming a clopidogrel hydrogen sulfate.

24. A method of inhibiting platelet aggregation, comprising administering an effective amount of a composition comprising clopidogrel hydrogen bromide hydrate as claimed in claim 1 to a patient in need thereof.

25. A method as claimed in claim 24, wherein the patient is a human.

26. A method as claimed in claim 24, wherein the amount of clopidogrel hydrogen bromide hydrate administered is from 10 mg to 125 mg with respect to the free base per day.

27. Clopidogrel hydrogen bromide anhydrate as claimed in any one of claims 2 or 3, wherein the clopidogrel hydrogen bromide anhydrate is in particulate form.

28. Clopidogrel hydrogen bromide anhydrate as claimed in any one of claims 2 or 3, wherein the clopidogrel hydrogen bromide anhydrate is substantially pure.

29. A process for preparing clopidogrel hydrogen bromide anhydrate as claimed in any one of claims 2 or 3, comprising the step of precipitating clopidogrel hydrogen bromide anhydrate from a solution of clopidogrel hydrogen bromide in an organic solvent.

30. A process as claimed in claim 29, further comprising the step of drying the precipitate.

31. A process as claimed in claim 30, wherein the drying step comprises vacuum drying.

32. A process as claimed in claim 31, wherein the drying step comprises vacuum drying at a vacuum of down to 50, 40, 35, 30, 25 or 20 mm Hg and at a temperature of up to 20, 25, 30, 35, 40, 45, 50, 55 or 60 ° C.

33. A process as claimed in claim 29, wherein the organic solvent is polar, miscible with water, dipolar, and/or aprotic.

34. A process as claimed in claim 29, wherein the organic solvent comprises a plurality or mixture of solvent compounds.

35. A process as claimed in claim 29, wherein the organic solvent is 2-propanol, diisopropyl ether, t-butylmethyl ether, dichloromethane, methanol, and/or ethanol.

36. A pharmaceutical composition, comprising clopidogrel hydrogen bromide anhydrate as claimed in any one of claims 2 or 3.

37. A pharmaceutical composition as claimed in claim 36, further comprising a pharmaceutically acceptable carrier, excipient or diluent.

38. A pharmaceutical composition as claimed in claim 36, wherein the composition is for oral administration.

39. A pharmaceutical composition as claimed in claim 36, wherein the composition is in the form of a tablet or capsule.

40. A pharmaceutical composition as claimed in claim 39, wherein the composition is in the form of a tablet and further comprises mannitol, macrogol, microcrystalline cellulose, hydrogenated castor oil, and/or low substituted hydroxypropylcellulose.

41. A pharmaceutical composition as claimed in claim 40, wherein the tablet is coated with hypromellose, lactose, triacetin, and/or carnauba wax.

42. A pharmaceutical composition as claimed in claim 36, wherein the composition is in unit dosage form comprising clopidogrel hydrogen bromide anhydrate in an amount of from 10 mg to 125 mg with respect to the free base.

43. A method of inhibiting platelet aggregation, comprising administering an effective amount of clopidogrel hydrogen bromide anhydrate as claimed in any one of claims 2 or 3 to a patient in need thereof.

44. A method as claimed in claim 43, wherein the patient is a human.

45. A method as claimed in claim 43, wherein the amount of clopidogrel hydrogen bromide anhydrate administered is from 10 mg to 125 mg with respect to the free base per day.

46. A process for preparing a polymorphic form of clopidogrel hydrogen sulfate, comprising the step of treating a clopidogrel hydrogen bromide anhydrate as claimed in any one of claims 2 or 3 with a chemical species to replace the bromide ion with a sulfate ion, thereby forming a clopidogrel hydrogen sulfate.

47. A method of inhibiting platelet aggregation, comprising administering an effective amount of a composition comprising clopidogrel hydrogen bromide anhydrate as claimed in any one of claims 2 or 3 to a patient in need thereof.

48. A method as claimed in claim 47, wherein the patient is a human.

49. A method as claimed in claim 47, wherein the amount of clopidogrel hydrogen bromide anhydrate administered is from 10 mg to 125 mg with respect to the free base per day.

\* \* \* \* \*

UNITED STATES PATENT AND TRADEMARK OFFICE
CERTIFICATE OF CORRECTION

PATENT NO. : 7,897,613 B2
APPLICATION NO. : 10/571419
DATED : March 1, 2011
INVENTOR(S) : Ramakrishnan Arul et al.

Page 1 of 1

It is certified that error appears in the above-identified patent and that said Letters Patent is hereby corrected as shown below:

In the Claims:

Claim 5, column 10 at lines 4-6, should read:

5. Clopidogrel hydrogen bromide hydrate as claimed in claim 1, wherein the clopidogrel hydrogen bromide hydrate is substantially pure.

Signed and Sealed this
Seventeenth Day of May, 2011

David J. Kappos
*Director of the United States Patent and Trademark Office*